(12) United States Patent
Park

(10) Patent No.: US 7,235,266 B2
(45) Date of Patent: Jun. 26, 2007

(54) FACIAL PACK AND BATHING COMPOSITIONS BASED ON HWANGTO (KOREAN LOESS) AND PREPARATION THEREOF

(76) Inventor: Jang Yong Park, 117-13(3/7), Kukidong, Jongroku, Seoul (KR)

(*) Notice: Subject to any disclaimer, the term of this patent is extended or adjusted under 35 U.S.C. 154(b) by 0 days.

(21) Appl. No.: 11/327,478

(22) Filed: Jan. 9, 2006

(65) Prior Publication Data

US 2006/0105058 A1    May 18, 2006

Related U.S. Application Data

(62) Division of application No. 10/965,883, filed on Oct. 18, 2004.

(51) Int. Cl.
*A61K 36/15*  (2006.01)
*A61K 36/16*  (2006.01)
(52) U.S. Cl. .................. 424/725.1; 424/770; 424/698; 424/752; 424/680

(58) Field of Classification Search ...................... None
See application file for complete search history.

*Primary Examiner*—Susan Hoffman
*Assistant Examiner*—Catheryne Chen
(74) *Attorney, Agent, or Firm*—Troxell Law Office, PLLC

(57) ABSTRACT

Disclosed are a facial pack composition and a bathing composition based on loess, and methods for preparing the same. The bathing composition makes a user feel refreshed, prevents arteriosclerosis and fat accumulation in human bodies, is useful for the treatment of maturating diseases such as dermatophytosis and dermatitis and stimulates metabolism and blood circulation system of the human body. Additionally, the facial pack includes loess having a fine particle size sufficient to avoid skin irritation and thus does not adversely affect the skin even if the user uses the pack everyday. The loess is pretreated by a unique aging method and selected additives, so that the far infrared ray-emitting effect of the loess can be maximized. Therefore, it provides skin health-aid and cosmetic effects. Further, the bathing composition is an environmental-friendly composition because the loess-containing water discharged after bathing flows into a draining path, thereby purifying a contaminated river and recovering contaminated soil.

2 Claims, No Drawings

FACIAL PACK AND BATHING COMPOSITIONS BASED ON HWANGTO (KOREAN LOESS) AND PREPARATION THEREOF

RELATED APPLICATIONS

This application is a Division of currently pending application U.S. Ser. No. 10/965,883, entitled "FACIAL PACK AND BATHING COMPOSITIONS BASED ON HWANGTO (KOREAN LOESS) AND PREPARATION METHOD" and filed on Oct. 18, 2004.

BACKGROUND OF THE INVENTION

FIELD OF THE INVENTION

The present invention relates to a facial pack composition and a bathing composition based on Korean loess, and methods for preparing the same.

In the present invention, by Korean loess it means one produced in South Korea and is also referred to as "Hwangto".

More particularly, the loess used in the present invention is obtained by pulverizing loess which is completely sun-dried into a size of 200–250 mesh; introducing the pulverized loess in an earthenware container together with pine tree charcoal, a paulownia wood material, alum and ginkgo leaves; sealing the earthenware container; and aging the materials at a temperature of −5 to 40° C. for 1 month to 6 months. The bathing composition including the loess obtained as described above has advantages in that it makes a user feel refreshed; it can prevent arteriosclerosis and fat accumulation in the human body; it is useful for the treatment of maturating diseases such as dermatophytosis and dermatitis; and in that it stimulates metabolism and blood circulation system. Additionally, according to the present invention, the facial pack includes loess having a fine particle size sufficient to avoid skin irritation, and thus does not adversely affect the skin even if the user uses the pack everyday. The loess used in the present invention is pre-treated by a unique aging method and selected additives, so that the far infrared ray-emitting effect of loess can be maximized. Therefore, it provides skin health-aid and cosmetic effects. Further, the bathing composition according to the present invention is characterized by the fact that it is an environmental-friendly composition, because the loess-containing water discharged after bathing flows into a draining path, thereby purifying a contaminated river and recovering contaminated soil. Meanwhile, the loess-containing composition according to the present invention may further comprise functional additives such as natural bay salt, extraction essence of pine buds, etc.

DESCRIPTION OF THE PRIOR ART

As generally known in the art, a conventional bathing preparation is prepared by combining a fragrant agent, a coloring agent, botanical aroma, an organic acid, etc. with a mixture composed of a salt cake such as crystalline sodium sulfonate, boric acid including sodium borate, an inorganic salt such as a carbonate and sulfur. Such conventional bathing preparations are used for the purpose of manifesting fragrance and colors to bathing water, and stimulating skin and blood circulation adequately, thereby promoting recovery from fatigue and stimulating metabolism.

Meanwhile, spas scattered in various regions in Korea are classified into radioactive spas, sulfur spas, acidic spas, etc., according to the characteristics of their water veins and qualities and their mineral contents. Such spas are used as cold spas and hot spas and are useful for the treatment of various diseases. As described above, spas have various functions and characteristics and thus consumers have to travel inconveniently from place to place in order to use a spa conformed to a desired purpose. To solve this inconvenience, the present invention provides a bathing composition including loess and/or extraction essence of pine leaves and natural salt so as to make consumers enjoy a "medical bath" with ease in their homes. The aforementioned constitutional elements and contents thereof including effects obtained thereby have remained undiscovered heretofore.

Meanwhile, with regard to a facial pack containing loess, cosmetics containing loess are described in U.S. Pat. No. 6,254,858 and Korea Patent Laid-Open No. 1999-0086959. However, the cosmetics according to the prior art are merely characterized by comprising loess. Moreover, there is no description with reference to the loess pre-treated by a unique method according to the present invention. Particularly, conventional cosmetics containing loess merely treated by the steps of washing, heating and particle selection cannot provide excellent effects of loess to the skin of a user. Therefore, such conventional cosmetics have no special effect.

SUMMARY OF THE INVENTION

Most conventional bubble type bathing preparations include alkaline carbonates, and thus carbon dioxide gas generated as bubbles in water are not completely decomposed nut are volatilized in the air. Therefore, such conventional bathing preparations have only sensual functions. Moreover, fragrance added to the bathing preparations has great volatility, and thus evaporates according to the occurrence of expansion of carbon dioxide gas. Therefore, the effects of fragrance itself cannot be exploited satisfactorily. Additionally, because a bathing preparation, as it is, is a kind of surfactant, it may cause environmental pollution when discharged into a draining path after bathing. Accordingly, the present invention has been made to solve the above-mentioned problems occurring in the prior art and an object of the present invention is to provide a bathing composition including natural materials by combining each of constitutional elements in such an amount that the effect of each element can be maximized. The bathing composition according to the present invention can greatly satisfy the users during and after bathing.

Additionally, the facial pack according to the present invention using loess pre-treated by a unique process can solve the problem of skin irritation occurring in the prior art. The facial pack according to the present invention has an additional effect of skin softening. Further, it is useful for the treatment of facial skin diseases, etc.

In order to accomplish this object, there is provided a bathing composition obtained by preparing loess powder and/or natural salt, and extraction essence of pine buds (referred as constitutional elements of the bathing composition according to the present invention), individually and mixing them in a predetermined ratio. The bathing composition of the present invention takes the form of powder to be added in a predetermined amount to a bathtub for bathing.

Because each of the constitutional elements of the present invention is prepared individually, each element can form an individual invention and only a part of the constitutional elements of the present invention can be added to a bathtub for bathing. Additionally, the facial pack composition according to the present invention is formed of loess powder and/or natural salt and extraction essence of pine buds. Particularly, the loess used in the facial pack composition is thoroughly pre-treated so as to obtain the maximized effect of loess.

Hereinafter, each of the constitutional elements of the cosmetic and bathing compositions will be explained in detail.

Loess Powder

The present invention is characterized by pre-treatment process of loess. In other words, the technical gist of the present invention is that loess pre-treated by a unique process is used in a facial pack or a bathing composition.

Preferably, loess of good quality that exists at a depth of 90 cm or less from the surface is used. Loess is a silicon-containing mineral substance subjected to sunlight energy for a long duration and is characterized by emitting far infrared rays and anions. Additionally, it stimulates metabolism by the effect of active yeasts and is useful for the prevention of aging and adult diseases. Loess includes fine sand and a great amount of calcium carbonate, is not brittle, has a high viscosity and is transformed into clay when kneaded with water. In a spoon of loess, about 200 millions of microorganisms live and various enzymes circulate. Therefore, loess has been known as a living body since early times.

Loess emits a great amount of far infrared rays and includes beneficial enzymes such as a catalase, diphenol oxydase, saccharase and protease, wherein the enzymes can remove toxins, give degradability, act like a fertilizer and purify soil.

When a human body shows aging phenomena according to the occurrence of oxidized lipid toxins during the metabolic process, the catalase, which is a microorganism present in loess, can neutralize and dilute the toxins, thereby preventing skin aging. The protease hydrolyzes proteins into amino acids when nitrogen in the proteins is mineralized, and thus decomposes and breaks a carcinoma, a tumor and other pathogens and detoxifies a purulent wound and body toxins.

The loess powder used in the present invention is prepared as follows.

In a designated loess production source location, soil on the surface is removed and loess of good quality that exists in a depth of 90 cm or less from the surface is collected. The collected loess is pulverized in a pulverizer. In order to remove toxins, the pulverized loess powder is distributed on a floor in a thin and uniform state and then is naturally dried. The dried loess powder is introduced into a loess-producing machine to remove foreign materials such as stones, and then the loess is further dried by heating with sunlight. Such a natural drying method is different from a conventional drying method in the prior art that uses a mechanical heating means. Next, the naturally dried loess is further introduced into a loess powder-producing machine to remove fine foreign materials and to obtain fine powder. The fine powder of loess is naturally dried by heating with sunlight and then is introduced into a pulverizer to produce powder having a main particle size of 150–200 mesh. The loess powder having such a size may be used in a bathing composition. Further, the loess powder is introduced again into a pulverizer to produce powder having a main particle size of 250–1,000 mesh, more preferably about 1000 mesh, the powder being used in a facial pack that is a cosmetic composition according to the present invention. Then, such dried loess powder is aged. In the aging step, dried loess powder is introduced into an earthenware container and the earthenware container is sealed to perform aging for 1 month to 6 months. To the earthenware container, pine tree charcoal, a paulownia wood material, alum and ginkgo leaves, wrapped in a coarse gauze web, may further be added. We have found that aging the loess for 4 weeks or more at −5° C. to 40° C. can remarkably improve the far infrared ray-emitting activity of loess. On the other hand, loess aged only for 1–2 weeks has been used according to the prior art. By aging loess under the above-described conditions, the loess used in the present invention acts as "living loess" in contrast with loess according to the prior art, and thus provides maximized functions of loess when used in the composition according to the present invention.

Natural Salt

Salt used in the present invention is bay salt, which is prepared by drawing seawater into a salt farm, heating and evaporating it with sunlight and concentrating into salt. This bay salt contains a great amount of mineral substances, because seawater mixed with mud is evaporated by heating with sunlight while harmful substances is removed with the wind. Distinguishing salt of good quality from salt of poor quality is done by the naked eye. Salt of good quality has square-shaped particles obtained by being subjected to sunlight at high noon. Salt of poor quality has hexahedral particles obtained by being subjected to the wind at night, and thus is toxic. Salt used in the present invention is bay salt having square-shaped particles, which is detoxified, purified and finely divided by heating at a high temperature (1000° C.) for 1 hour or more.

Only the salt freshly produced by using seawater of good quality on the soil in a salt farm at a sunny day under a controlled water temperature of 30° C. is used in the present invention. Natural bay salt has a property capable of degrading fats and oils. Natural salt accelerates physiological functions of skin and skin respiration, thereby acting like a good soap, shampoo, rinse, treatment and lotion. Therefore, it is possible to make skin care and hair care products having the best quality. Additionally, natural salt is a supplementary substance for natural hair-maintaining and hair-caring agents. Further, salt has detoxifying and sterilizing activities, and thus increases the resistance of a human body against attack of harmful matters or bacteria so as to protect them from penetrating into cells and blood vessels. The bay salt used in the present invention is prepared as follows. Seawater mixed with mud is evaporated under sunlight with the wind to obtain bay salt. Then, the bay salt is maintained on the soil in a salt farm under a controlled water temperature of 25–35° C. Only the salt, which is freshly produced, is collected. In Korea, salt produced from a salt farm located in the west seashore is regarded as the best. Therefore, such salt having the best quality is taken by an order. The natural bay salt is introduced into a heat processor of salt in an amount of 5–15 kg and is heated at a temperature of 300–400° C. for about 1 hour. By doing so, it is possible to remove moisture and toxic arsenic from bay salt. Thus prepared bay salt has a particle size of about 100 mesh. Such baked salt is introduced again into a pulverizer to further pulverize it. Finally, the pulverized salt has a particle size of about 200 mesh.

Extraction Essence of Pine Buds

The deep green light of pine leaves results from terpene contained in the essence, terpene being also present in main components of pine resin. Terpene contains a great amount of unsaturated fatty acids. A pine tree contains tonic agents based on terpentin, Vitamin A, Vitamin C, chlorophyll, etc., including alcohols, esters, phenolic compounds and glycogenin. Among these, alcohols and esters have a function for discharging waste products, thereby further stimulating metabolism. Vitamin A has a function for strengthening mucous membranes. Glycogenin has a function for dropping blood sugar, and thus is useful for treating diabetes. Black pine trees and red pine trees contain a great amount of Vitamin C, and quercetin contained in Vitamin C is effective for dropping blood pressure. Pine tree concentrate can remove cholesterol. Hyperlipidemia, which is a disease including a increase of fat contents in blood, results from eating habits of Europe and America related with intake of a great amount of animal fat contents, and is responsible for arteriosclerosis, cerebral infarction, heart attack and myocardial infarction. Bathing in a pine-leaf bath is effective in cold hypersensitivity, neuralgia, blood anemia, neurogastritis, etc., because Vitamin A, Vitamin C, palmitic acid, stearic acid, etc., can stimulate blood circulation. Extract of pine leaves used in the present invention is prepared as follows.

Pine buds spring up freshly at early in March to May. Pine buds having a length of about 5 cm are cut and washed with water to remove dust. The washed pine leaves are dried and heated with hot steam. By collecting water steam, extracted essence of pine buds can be obtained. The extraction essence is collected to be used in the present invention.

Hitherto, each constitutional element of the composition according to the present invention has been fully explained. Mixing of the constitutional elements of the composition according to the present invention will be explained hereinafter.

0.5 to 3 parts by weight of the extraction essence of pine buds based on 10 parts by weight of natural salt is introduced into a mixer. Both materials are mixed for about 10 to 50 minutes. The mixture is further mixed with 30 to 50 parts by weight of loess powder. The resultant mixture is introduced into a packing container and then tightly sealed with a vinyl sealer so as not to leak pine aroma.

Uses and effects of the bathing composition according to the present invention will be explained hereinafter.

It is advisable to take a half-body bath, wherein 100–300 g of the bathing composition is added to water of about 38–40° C. filled to one half of the depth of a bathtub. In bathing, a part of the user's body corresponding to the part under the breast may be dipped in water. After the user's body is covered with sweat by taking a bath for about 10–15 minutes, the user may come out of the bathtub. In the case of massaging the whole body, loess powder may be taken in an adequate amount and kneaded with water in a container. Then, the kneaded loess powder may be applied to the whole body with a hand or a brush. After about 15 minutes, users can feel tightness. In this time, users may bathe again. By doing so, it is possible for users to enjoy a natural pine-leaf bath while unique pine aroma is harmonized with the loess. After 10–15 minutes, users may take a shower with clean water to complete the pine-leaf bath process.

When the facial pack according to the present invention is used, users preliminarily remove facial make-up cleanly, wash their faces and apply a skin toner on their faces. Next, 1–2 spoons (about 10 g) of the facial pack composition is mixed well to obtain a creamy phase and the pack composition is applied on the face or neck. When users feel tightness after a lapse of about 10 minutes, the pack may be washed out by using soap or a foam cleanser.

Additionally, the loess powder according to the present invention may be applied as a cosmetic material in addition to a facial pack or a bathing composition. For example, by adding the loess powder into a cosmetic soap, a loess-containing soap can be obtained. More particularly, in order to make a soap base, oils and fats are hydrolyzed into fatty acids and glycerol and then the fatty acids are neutralized with sodium hydroxide or sodium carbonate. To the soap base, the loess powder according to the present invention and, if desired, conventional additives such as an anti-oxidant, a coloring agent, fragrance, an irritation-alleviating agent, a builder for increasing cleansing power (for example, condensed sodium phosphate, sodium carbonate and sodium silicate), etc., are added and stirred for 30 minutes. The resultant materials are then introduced into a cooling mold by using a mold mastication method or a mechanical mastication method using net with 100 mesh, pulverized more than three times, cooled and solidified. Further, the solidified materials are cut, dried for 3 days, formed into a desired shape, and then packaged as a commercial product.

DETAILED DESCRIPTION OF THE PREFERRED EMBODIMENTS

Reference will now be made in detail to the preferred embodiments of the present invention. The following examples are illustrative only and the scope of the present invention is not limited thereto.

EXAMPLE 1-1

Preparation of Loess Powder

Loess of good quality, which exists in a depth of 90 cm or less from the surface in a designated loess production place, was collected. The collected loess was pulverized in a pulverizer. The pulverized loess powder was distributed on a floor in a thin and uniform state and then was naturally dried with sunlight. The naturally dried loess powder was introduced into a loess-producing machine to remove foreign materials such as stones, and then further dried by heating with sunlight. Next, the naturally dried loess was introduced again into a loess powder-producing machine to remove fine foreign materials and to obtain fine powder. The fine powder of loess was naturally dried by heating with sunlight and then was introduced again into a pulverizer to produce powder having a main particle size of 200 mesh. Then, the dried loess powder was introduced into an earthenware container. To the earthenware container, 5 parts by weight of pine tree charcoal, 5 parts by weight of a paulownia wood material, 5 parts by weight of alum and 5 parts by weight of ginkgo leaves, based on 100 parts by weight of the loess, were added. The mixture was aged at 10° C. for 6 months. Further, the loess powder was introduced again into a pulverizer to produce powder having a main particle size of 300 mesh. Additionally, the powder was pulverized into a size of about 1,000 mesh so as to be used in a facial pack composition.

EXAMPLE 1-2

Preparation of Loess Powder

Example 1-1 was repeated to prepare loess powder, except that the loess powder was aged at 10° C. for 1 month.

EXAMPLE 1-3

Preparation of Loess Powder

Example 1-1 was repeated to prepare loess powder, except that the loess powder was aged at 10° C. for 2 months.

EXAMPLE 1-4

Preparation of Loess Powder

Example 1-1 was repeated to prepare loess powder, except that the loess powder was aged at 10° C. for 3 months.

EXAMPLE 1-5

Preparation of Loess Powder

Example 1-1 was repeated to prepare loess powder, except that the loess powder was aged at 10° C. for 4 months.

EXAMPLE 1-6

Preparation of Loess Powder

Example 1-1 was repeated to prepare loess powder, except that the loess powder was aged at 10° C. for 5 months.

COMPARATIVE EXAMPLE 1-1

Example 1-1 was repeated to prepare loess powder, except that the loess powder was not naturally dried but mechanically dried.

COMPARATIVE EXAMPLE 1-2

Example 1-1 was repeated to prepare loess powder, except that the loess powder was aged at 10° C. for 1 week.

COMPARATIVE EXAMPLE 1-3

Example 1-1 was repeated to prepare loess powder, except that the loess powder was aged at 10° C. for 2 weeks.

COMPARATIVE EXAMPLE 1-4

Example 1-1 was repeated to prepare loess powder, except that the loess powder was aged at 10° C. for 3 weeks.

COMPARATIVE EXAMPLE 1-5

Example 1-1 was repeated to prepare loess powder, except that the loess powder was aged at 10° C. for 7 months.

EXAMPLE 2

Preparation of Natural Salt 10 kg of natural bay salt was introduced into a salt heater and heated at 350° C. for 1 hour. Particles having a size of about 100 mesh were obtained. 10 kg of the baked salt was introduced into a pulverizer and then pulverized again. Final natural salt was obtained by screening with a 200-mesh sieve.

EXAMPLE 3

Preparation of Extraction Essence of Pine Buds

Pine buds appearing freshly at early in March to May and having a length of about 5 cm were cut and washed with water to remove dust. The washed pine leaves were dried and heated with hot steam. By collecting water steam, extraction essence of pine buds was obtained. The extraction essence was collected to be used in this example. In this example, a distillation method with water steam was used, but a fatty oil extraction method, an expression method, etc., may be used.

EXAMPLE 4

Preparation of Bathing Composition 10 kg of the natural salt and 1.5 kg of the extraction essence of pine buds were introduced into a mixer and mixed for about 20 minutes. The mixture was mixed with 40 kg of the loess powder having a size of 200 mesh (loess powder according to Examples 1-1 to 1-6). The resultant mixture was introduced into a packing container and sealed so as not to leak pine aroma, thereby providing a final product.

EXAMPLE 5

Preparation of Facial Pack Composition 10 kg of the natural salt and 1.5 kg of the extraction essence of pine buds were introduced into a mixer and mixed for about 20 minutes. The mixture was mixed with 40 kg of the loess powder having a size of 1,000 mesh (loess powder according to Examples 1-1 to 1-6). The resultant mixture was introduced into a packing container and sealed so as not to leak pine aroma, thereby providing a final product.

COMPARATIVE EXAMPLE 2

Preparation of Bathing Composition

Example 4 was repeated to prepare a bathing composition, except that the loess powder according to Comparative Examples 1-1 to 1-5 was used.

COMPARATIVE EXAMPLE 3

Preparation of Facial Pack Composition

Example 5 was repeated to prepare a facial pack composition, except that the loess powder according to Comparative Examples 1-1 to 1-5 was used.

EXAMPLE 6

Experimental Example 100 persons were selected to perform an experiment by using the compositions as described above with regard to skin irritation, waste product discharging effects, moisturizing effects, healing of skin troubles, etc. The results are shown in Table 1. In table 1, each of designated number represents the number of Example or Comparative Example, from which the corresponding composition is obtained.

TABLE 1

| No. | Skin irritation | Waste product discharging | moisturizing | Skin trouble healing |
|---|---|---|---|---|
| Examples |  |  |  |  |
| 1-1 | ☆ | ☆ | ☆ | ☆ |
| 1-2 | ☆ | ☆ | ☆ | ☆ |
| 1-3 | ☆ | ⊙ | ⊙ | ☆ |
| 1-4 | ☆ | ⊙ | ⊙ | ☆ |
| 1-5 | ☆ | ⊙ | ⊙ | ☆ |
| 1-6 | ☆ | ☆ | ☆ | ☆ |
| Comparative Examples |  |  |  |  |
| 1-1 | X | X | X | X |
| 1-2 | X | ◊ | X | ◊ |
| 1-3 | X | ◊ | X | ◊ |
| 1-4 | O | ◊ | X | ◊ |
| 1-5 | O | O | ⊙ | ◊ |

☆: excellent
⊙: good
O: not bad
◊: ineffective
X: very poor

As shown in Table 1, the facial pack using the loess powder according to the present invention generates less skin irritation, shows excellent cleansing effect and moisturizing effect, and is effective for healing dermatitis, in contrast with conventional facial pack compositions using conventional loess that is not aged under conditions according to the present invention.

As can be seen from the foregoing, the bathing composition according to the present invention has advantages in that it makes a user feel refreshed due to the pine aroma; it can prevent arteriosclerosis and fat accumulation in the human body by virtue of the terpene which contains unsaturated fatty acids; it can supplement anions by virtue of natural salt; it is useful for the treatment of maturating diseases such as dermatophytosis and dermatitis; and in that it stimulates metabolism and the human blood circulation system by the far infrared ray-emitting activity of loess. Additionally, the bathing composition according to the present invention is an environmental-friendly composition, because the loess-containing water discharged after bathing flows into a draining path, thereby purifying a contaminated river and recovering contaminated soil. Further, the facial pack according to the present invention has excellent moisturizing effect, generates less skin irritation and can removes sebaceous matters from the user's facial skin, thereby maintaining skin in a clean state, irrespective of oily and dry skin.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A method for preparing a bathing composition, comprising the steps of:
  (a) pulverizing natural loess that is completely sun-dried into a size of 200–250 mesh, introducing the pulverized loess in an earthenware container together with pine tree charcoal, a paulownia wood material, alum and ginkgo leaves, sealing the earthenware container and aging the materials at a temperature of −5 to 40° C. for 1 month to 6 months to produce a loess containing powder;
  (b) heating natural bay salt at a temperature of about 300–400° C. for 1–2 hours;
  (c) drying pine buds, heating them with steam and collecting water steam to extract a distilled essence of pine buds;
  (d) introducing the bay salt and the distilled essence of pine buds into a mixer and mixing them for 10–50 minutes, wherein the amount of the bay salt is 10 parts by weight per 30–50 parts by weight of the loess and the amount of the distilled essence of pine buds is 0.5–3 parts by weight per 30–50 parts by weight of the loess; and
  (e) mixing the mixture obtained from step (d) with said 30–50 parts by weight of the loess containing powder and agitating them in a kneader for 10–50 minutes.

2. A method for preparing a facial pack composition, comprising the steps of:
  (a) pulverizing natural loess that is completely sun-dried into a size of about 1,000 mesh, introducing the pulverized loess in an earthenware container together with pine tree charcoal, a paulownia wood material, alum and ginkgo leaves, sealing the earthenware container and aging the materials at a temperature of −5 to 40° C. for 1 month to 6 months to produce a loess containing powder;
  (b) heating natural bay salt at a temperature of about 300–400° C. for 1–2 hours;
  (c) drying pine buds, heating them with steam and collecting water steam to to extract a distilled essence of pine buds;
  (d) introducing the bay salt and the distilled essence of pine buds into a mixer and mixing them for 10–50 minutes, wherein the amount of the bay salt is 10 parts by weight per 30–50 parts by weight of the loess and the amount of the distilled essence of pine buds is 0.5–3 parts by weight per 30–50 parts by weight of the loess; and
  (e) mixing the mixture obtained from step (d) with said 30–50 parts by weight of the loess containing powder and agitating them in a kneader for 10–50 minutes.

* * * * *